United States Patent [19]

Whitney

[11] Patent Number: 4,909,826

[45] Date of Patent: Mar. 20, 1990

[54] METHOD FOR CONTROLLING *CAPERONIA PALUSTRIS* WITH THE FUNGUS *AMPHOBOTRYS RICINI*

[75] Inventor: N. Glenn Whitney, Beaumont, Tex.

[73] Assignee: Texas A&M University, College Station, Tex.

[21] Appl. No.: 206,032

[22] Filed: Jun. 13, 1988

Related U.S. Application Data

[63] Continuation of Ser. No. 10,747, Feb. 4, 1988, abandoned.

[51] Int. Cl.$^4$ .............................................. A01N 63/04
[52] U.S. Cl. .......................................................... 71/79
[58] Field of Search ............................................. 71/79

[56] References Cited

U.S. PATENT DOCUMENTS 3,999,973  12/1976  Templeton ............................. 71/79

OTHER PUBLICATIONS

Whitney et al, Plant Disease 70:892 (1986).
Wilson, Ann. Rev. Phytopathol. 7:411–434 (1969).
Daniel et al, Weed Science 21:303–307 (1973).
Templeton et al, Tropical Pest Management 30(4):333–338 (1984).
Templeton et al, Plant Disease: An Advanced Treatise 1, 167–176 (1977).
Templeton et al, Ann. Rev. Phytopathol. 17:301–310 (1979).
Hennebert, Persoonia 7:183–204 (1973).

*Primary Examiner*—Robert V. Hines
*Attorney, Agent, or Firm*—Arnold, White & Durkee

[57] ABSTRACT

The invention relates to the use of the fungus *Amphobotrys ricini* as a mycoherbicide to control texasweed (*Caperonia palustris*). *Amphobotrys ricini* has been found to infect and kill texasweed when applied to the plant and is considered effective at all stages of plant development.

9 Claims, No Drawings

METHOD FOR CONTROLLING *CAPERONIA PALUSTRIS* WITH THE FUNGUS *AMPHOBOTRYS RICINI*

This is a continuation of application, Ser. No. 010,747, filed Feb. 4, 1988.

The invention relates to the use of the fungus *Amphobotrys ricini* as a mycoherbicide to control texasweed (*Caperonia palustris*). *Amphobotrys ricini* has been found to infect and kill texasweed when applied to the plant and is considered effective at all stages of plant development.

BACKGROUND OF THE INVENTION

Texasweed (*Caperonia palustris*) is a weed known to affect rice and soybean crops throughout the Gulf Coast region of the United States. This weed, unfortunately, has been found to be extremely difficult to control. Currently available chemical herbicides, for example, are only effective against very small texasweed. Once texasweed has grown past the seedling stage, it is almost impossible to control using conventional herbicides.

Increased emphasis has been placed on the development of what are known as mycoherbicides. These involve the use of natural pathogens to control weeds. A fungus known to infect a weed is selected and cultured. The pathogen is then applied to the weed and allowed to normally infect the plant and kill it. The pathogen selected is one which does not affect the crop infested with the weed to be controlled.

An example of the use of mycoherbicides is the use of the fungus *Colletotrichum gloeosporioides* to control northern jointvetch (*Aeschynomene virginica*) in Arkansas rice and soybean production. This fungus is a known pathogen of northern jointvetch but does not affect the rice or soybean crops. The fungus is applied to this weed in an aqueous suspension.

One disadvantage with mycoherbicides is that the pathogens are generally specific for one variety or strain of weeds. Until now, no such mycoherbicide has been found which is effective in controlling texasweed.

SUMMARY OF THE INVENTION

The present invention lies in the use of the fungus *Amphobotrys ricini* to control texasweed. This fungus has been known to infect at least one member of the spurge family of plants but, to date, it has not been reported to infect texasweed. It has recently been discovered, however, that *Amphobotrys ricini* can infect texasweed and other members of the spurge family without affecting surrounding crops, such as rice or soybean plants. One aspect of the present invention, accordingly, involves the culturing of *Amphobotrys ricini*, harvesting the fungus and then applying the fungus to the texasweed and permitting normal infection to occur.

DETAILED DESCRIPTION OF THE INVENTION

Pursuant to the present invention, *Amphobotrys ricini* was isolated from black sclerotia embedded in the stem tissue of dead texasweed plants at the Texas A&M University Research and Extension Station in Beaumont, Texas. The fungus was grown on potato-dextrose agar at 23° C. until conidia growth occurred. In culture, the colonies were light gray and macroscopically similar to colonies of Botrytis but was identified as *Amphobotrys ricini*.

The cultures were allowed to grow until conidia were formed. The conidiaphores were long, slender, pigmented and highly branched, with clusters of conidia at the apex of each branch. The conidia were ovoid, one-celled and hyaline. The conidia were then harvested and used to infect texasweed growing in a crop of soybeans.

It has been found that the fungus can be applied successfully to texasweed according to either of two methods. First, the fungus may be inoculated into the weed at a specific site. This has been accomplished by transferring the conidia using a toothpick as a probe to inoculate the stem of the plant. Within three days of inoculation, stem cankers formed at the inoculation sites. The cankers enlarged and eventually girdled the stems. Within two weeks, the entire plant was killed.

A second and preferred method for applying Amphobotrys as a mycoherbicide has been to spray a suspension of the conidia on the weeds to be controlled. In practicing this method, the conidial portions of the fungus were harvested and suspended in water at a concentration of 4,000 conidia per milliliter. The suspension was then sprayed in the mid-afternoon over a field of soybeans infested with texasweed. Stem cankers began appearing within three days of infection. Weeds were killed within two weeks after the spraying. No adverse effect was noted on the soybeans in the sprayed field.

Environmental conditions may, of course, affect the use of *Amphobotrys ricini* as a mycoherbicide. Thus, the herbicide should be applied in conditions suitable for the growth of the fungus. Preferably, the ambient temperature should be in the range of about 16° C. to about 30° C. . Sufficient moisture should be present in the air and field to provide proper conditions for the growth of the fungus. As rice crops are generally grown in moist fields and conditions, the humidity requirement for treating texasweed is generally met without the need for additional water or concern for administration conditions. In any event, the environmental conditions that will be required will be readily apparent to those skilled in the art.

It will be apparent that a number of variations in the forgoing invention may be practiced without departing from the scope or spirit of the invention. It is contemplated, for example, that cultures of the fungus can be grown on shredded texasweed. The conidia may be mixed with inert materials which do not adversely affect the fungus to aid in handling and distribution.

What is claimed is:

1. A method for controlling the weed *Caperonia palustris* which comprises infecting the weed with a herbicidally effective amount of the fungus *Amphobotrys ricini*.

2. The method in claim 1 wherein the infecting is performed by inoculating said weed with said fungus.

3. The method of claim 2 wherein the inoculation is accomplished by placing the conidia of said fungus on the tip of a probe and inserting said probe into the stem of said weed.

4. The method of claim 1 wherein said infecting is performed by spraying said weed with a liquid suspension of the conidia of said fungus.

5. The method of claim 4 wherein spraying is performed at a temperature between about 16° C. and 30° C.

6. The method of claim 4 in which the suspension is an aqueous suspension.

7. The method of claim 6 wherein said conidia *Amphobotrys ricini* is suspended in said aqueous suspension at a concentration of 4,000 conidia per milliliter.

8. A herbicidal composition comprising an aqueous suspension which contains a herbicidally effective concentration of the conidia of the fungus Amphobotrys ricini.

9. The herbicidal composition of claim 8, wherein the concentration of the conidia in the aqueous suspension is at least 4,000 conidia per milliliter.

* * * * *

UNITED STATES PATENT AND TRADEMARK OFFICE
CERTIFICATE OF CORRECTION

PATENT NO. : 4,909,826
DATED : March 20, 1990
INVENTOR(S) : Whitney, et al.

It is certified that error appears in the above-identified patent and that said Letters Patent is hereby corrected as shown below:

In column 1, line 7, "1988" should be --1987--.

In column 2, line 1, "Botrytis" should be italicized.

In column 2, lines 19-20, "Amphobotrys" should be italicized.

In column 4, lines 1 and 2, "Amphobotrys ricini" should be italicized.

Signed and Sealed this

Fourth Day of June, 1991

Attest:

HARRY F. MANBECK, JR.

*Attesting Officer*  *Commissioner of Patents and Trademarks*